US012797503B2

(12) United States Patent
Johnson et al.

(10) Patent No.: US 12,797,503 B2
(45) Date of Patent: Nov. 17, 2026

(54) PASSIVE EMANATOR, ESPECIALLY A FRAGRANCE EMANATOR

(71) Applicant: Reckitt & Colman (Overseas) Hygiene Home Limited, Slough (GB)

(72) Inventors: Andrew Johnson, Hull (GB); Akira Naidu, Hull (GB); Jake Stephen Williams, Hull (GB)

(73) Assignee: VEH IP UK LIMITED, Berkshire (GB)

(*) Notice: Subject to any disclaimer, the term of this patent is extended or adjusted under 35 U.S.C. 154(b) by 425 days.

(21) Appl. No.: 18/552,748

(22) PCT Filed: Mar. 23, 2022

(86) PCT No.: PCT/GB2022/050728
§ 371 (c)(1),
(2) Date: Sep. 27, 2023

(87) PCT Pub. No.: WO2022/208053
PCT Pub. Date: Oct. 6, 2022

(65) Prior Publication Data

US 2024/0165290 A1 May 23, 2024

(30) Foreign Application Priority Data

Apr. 1, 2021 (EP) .................................... 21166548
Apr. 1, 2021 (GB) .................................... 2104706

(51) Int. Cl.
*A61L 9/12* (2006.01)
*A01M 1/20* (2006.01)
*A61L 9/04* (2006.01)

(52) U.S. Cl.
CPC ........... *A61L 9/127* (2013.01); *A01M 1/2044* (2013.01); *A61L 9/044* (2013.01); *A61L 9/122* (2013.01)

(58) Field of Classification Search
CPC ........................................................ A61L 9/27
See application file for complete search history.

(56) References Cited

U.S. PATENT DOCUMENTS 10,149,917 B2 12/2018 Webb et al.
10,507,257 B2 12/2019 Yeung et al.
(Continued)

FOREIGN PATENT DOCUMENTS

CN 1396835 A 2/2003
CN 112074300 A 12/2020
(Continued)

OTHER PUBLICATIONS

International Search Report and Written Opinion of the International Searching Authority for corresponding application PCT/GB2022/050728 dated Jun. 8, 2022.
(Continued)

*Primary Examiner* — Kevin Joyner
(74) *Attorney, Agent, or Firm* — Norris McLaughlin, PA

(57) ABSTRACT

The passive emanator 2, especially for a fragrance, comprises a container 12 including a liquid composition 16 to be evaporated and emanated from the emanator via surrounding air, a porous wick 20 emerged in the liquid composition 16, and a porous membrane 18 arranged above a level of the liquid composition 16, wherein the membrane 18 is in contact with the wick 20 such that the membrane 18 is saturated with the liquid composition 16 via the wick 20 and an outer surface of the membrane 18 is in contact with the surrounding air. The liquid composition 16 includes a first solvent (especially DMM), a second solvent (especially DPM) and a fragrance or an insect repellent. The DMM and DPM are present in the liquid composition 16 at a weight ratio between 1:5 and 1:7, preferably 1:6, and most preferably 1:6.4.

11 Claims, 3 Drawing Sheets

(56) References Cited

U.S. PATENT DOCUMENTS

| | | | |
|---|---|---|---|
| 2005/0152935 | A1 | 7/2005 | Lang |
| 2005/0199742 | A1 | 9/2005 | Maat |
| 2007/0257130 | A1 | 11/2007 | Butler |
| 2013/0183261 | A1 | 7/2013 | Harada et al. |
| 2013/0230476 | A1 | 9/2013 | Pelzer et al. |
| 2018/0311395 | A1 | 11/2018 | Blondeau et al. |
| 2019/0345411 | A1 | 11/2019 | Blondeau et al. |
| 2021/0030913 | A1 | 2/2021 | Coals |

FOREIGN PATENT DOCUMENTS

| | | | |
|---|---|---|---|
| EP | 1078640 | A1 | 2/2001 |
| EP | 1552854 | A1 | 7/2005 |
| EP | 1313649 | B1 | 2/2008 |
| EP | 2005974 | A1 | 12/2008 |
| EP | 2272541 | A1 | 1/2011 |
| EP | 3106179 | A1 | 12/2016 |
| EP | 2629807 | B1 | 4/2017 |
| EP | 3409117 | A1 | 12/2018 |
| GB | 2181649 | A | 4/1987 |
| GB | 2423930 | A | 9/2006 |
| JP | 2006176700 | A | 7/2006 |
| WO | 0162308 | A1 | 8/2001 |
| WO | 03086490 | A1 | 10/2003 |
| WO | 2006114987 | A1 | 11/2006 |
| WO | 2007086035 | A1 | 8/2007 |
| WO | 2010070576 | A1 | 6/2010 |
| WO | 2007040157 | A1 | 4/2012 |
| WO | 2012043437 | A1 | 4/2012 |
| WO | 2013037665 | A1 | 3/2013 |
| WO | 20200028340 | A1 | 2/2020 |
| WO | 2020104009 | A1 | 5/2020 |

OTHER PUBLICATIONS

GB Search Report for corresponding application GB 2104706.3 dated Sep. 22, 2021.

Chinese Office Action in corresponding application CN 202280026891.0 dated Jan. 20, 2026, with English translation.

Extended European Search Report for corresponding application EP 21166548.4 dated Nov. 9, 2021.

PASSIVE EMANATOR, ESPECIALLY A FRAGRANCE EMANATOR

This is an application filed under 35 USC 371 based on PCT/GB2022/050728 filed on 23. Mar. 2022, which claimed priority to GB 2104706.3 filed 1. Apr. 2021, and EP 21166548.4 filed 1. Apr. 2021. The present application claims the full priority benefit of all prior applications and incorporates by reference their full disclosures as if set forth herein.

The present invention relates to controlled rate release devices for volatile materials, specifically liquids comprising a fragrance or an insect repellent. In particular, the invention relates to air fresheners operating on the principle of liquid phase transfer of a liquid fragrance composition through a porous membrane.

Air fresheners are known for the purpose of emanating odorising or deodorising active ingredients into the environment, such as a room in a house. Passive and active air fresheners are available. The latter emit the active ingredients at certain intervals, whereas the former rely on evaporation of volatile ingredients, e.g. at room temperature without the need of an external source of energy aiding the release of the active ingredients.

Many prior art passive air fresheners initially deliver a large amount of fragrance and subsequently deliver progressively less fragrance. The initial large dose is often “too much” and therefore objectionable, while the later dose is “not enough” and sometimes even not perceivable anymore.

It is an object of the invention to disclose an improved passive emanator. In particular, it is an object of the invention to provide a passive emanator exhibiting delivery of a fragrance at a uniform rate over an extended period of time.

The passive emanator according to the invention comprises a container including a liquid composition to be evaporated and emanated from the emanator via surrounding air, a porous wick emerged in the liquid composition, and a porous membrane arranged above a level of the liquid composition, wherein the membrane is in contact with the wick such that the membrane is saturated with the liquid composition via the wick and an outer surface of the membrane is in contact with the surrounding air. The liquid composition comprises first and second solvents and a fragrance or an insect repellent. The first solvent is Dipropylene Glycol Dimethyl Ether (DMM) and the second solvent is Dipropylene Glycol Monomethyl Ether (DPM). The inventors have found out that including DMM in the composition aids the desired uniform evaporation because of its high vapour pressure, which introduces an overall higher vapour pressure into the DMM/DPM mix. The weight ratio between DMM and DPM is between 1:5 and 1:7, preferably 1:6, and most preferably 1:6.4. The inventors have found out that such ratio very well supports an extended period of time of about 45-60 days during which the composition evaporates at a substantially uniform rate.

Such a passive system will deliver continuous, consistent fragrance emanation during the lifetime of the composition by employing a wick and a membrane (such as a pad) which can be incorporated into the container to deliver a substantially linear weight loss of the composition over an extended period of time of the composition life time. The wick is emerged in the composition and directs the composition to the membrane via capillary action to keep it saturated as long as the composition is not exhausted. The outer surface of the membrane is in contact with surrounding air and thus emanates the composition to it in a uniform manner over time.

In a preferred embodiment, the membrane covers the liquid composition such that the outer surface of the membrane is as big as the surface of the composition facing the surrounding air. In this embodiment, the outer surface of the membrane which is in contact with the surrounding air is the sole surface from which the composition evaporates. As there is no evaporation “leakage” from the composition below and factoring in the wick which keeps the membrane saturated, this embodiment will deliver an improved uniform emanation by supporting a linear weight loss of the composition over an extended period of time.

Flashpoint and Evaporation Rate of DPM and DMM:

1. Dowanol DPM®, dipropylene glycol methyl ether obtainable from Dow Chemicals having a flashpoint of 75° C. and an evaporation rate of 3.
2. Proglyde DMM®, dipropylene glycol dimethyl ether obtainable from Dow Chemicals having a flashpoint of 65° C. and an evaporation rate of 80.

The above evaporation rates are relative to n-butylacetate having an evaporation rate of 100; the figure for Proglyde DMM® was calculated as the molecular weight×vapour pressure (mm Hg at 20° C.).

Preferably, the first solvent is present in the liquid composition between 5% and 15% by weight, the second solvent is present in the liquid composition between 30% and 70% by weight and the fragrance or insect repellent is present in the liquid composition between 20% and 40% by weight, based on the total weight of the composition.

The wick and the membrane can comprise polypropylene (PP) and/or polyethylene (PE) fibres and are preferably hydrophobic such that a saturation of the membrane with only the composition is secured.

The passive emanator can further comprise a fan, wherein an airflow generated by the fan is directed at the membrane. Preferably, the fan is operable at different speeds. In this embodiment, the fan supports emanation of the evaporated composition into the surrounding air and the reach of the emanator can be increased. Furthermore, choosing different fan speeds supports the selection of different emanation rates.

In another embodiment, the container, the wick, the membrane and the fan are incorporated into a housing, wherein the housing has at least one inlet opening for attracting air and at least one outlet opening for directing the airflow generated by the fan to the environment.

In the following, the invention is described in more detail.

Figure 1:
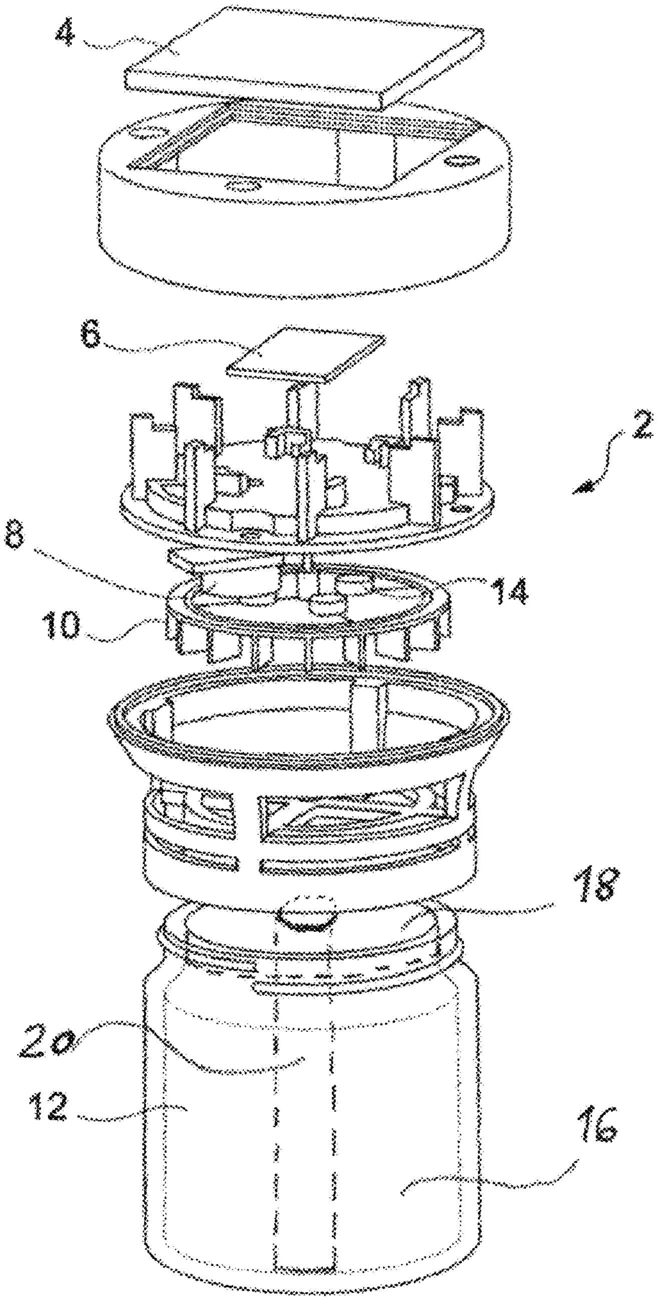
FIG. 1, shows an embodiment of a passive emanator according to the invention.

The figure shows an example of a passive emanator. The passive emanator 2 comprises a solar panel 4, a drive circuit 6, an electromagnet 8, a fan 10, at least one magnet 14 and a container 12 containing a volatile liquid composition.

The solar panel 4 is coupled to the drive circuit 6 which is connected to the electromagnet 8. The fan 10 is coupled to the at least one magnet 14. The fan 10 is located proximate to the electromagnet 8 so that the magnetic field generated by the electromagnet is sufficiently strong to attract or repel the at least one magnet 14. The fan 10 is located proximate to the container 12 so that the fan increases airflow and distribution of the volatile substance is increased.

In the example illustrated in the figure, the drive circuit is configured to receive power from the solar panel 4. The power received from the solar panel may be stored by the drive circuit using, for example, a battery. The power received from the solar panel 4 is used to drive the electromagnet 8 and the current driven through the electromagnet generates a magnetic field. The magnetic field can be altered by varying the magnitude and direction of the current. For example, the poles of the electromagnet 8 may be switched by changing the direction of the current.

The container 12 includes a liquid composition 16 to be evaporated by the emanator 2. A wick 20 is emerged in the liquid composition 16 and is in contact with a membrane 18, which can be a pad comprising PE and/or PP fibres. Also, the wick may comprise PE and/or PP fibres.

The wick 20 attracts the liquid composition 16 by capillary action and saturates the membrane 18 with the liquid composition 16.

The liquid composition 16 comprises a first solvent (Dipropylene Glycol Dimethyl Ether, DMM) and a second solvent (Dipropylene Glycol Monomethyl Ether, DPM). The DMM and DPM are present in the liquid composition at a weight ratio between 1:5 and 1:7, preferably 1:6, and most preferably 1:6.4. The liquid composition 16 further comprises a fragrance, which is present in the liquid composition between 20% and 40% by weight, based on the total weight of the composition.

The airflow generated by the fan 10 is directed at the membrane 18 so that the evaporating liquid composition 16 compromising the fragrance is distributed to the surrounding air through outlet openings of the emanator 2.

The fan 10 can be operated at different speeds such that the emanation rate of the emanator 2 can be adjusted as desired.

Examples of five liquid compositions suitable for use with an emanator as shown before are:

| | Weight % | | | | |
|---|---|---|---|---|---|
| DMM | 10 | 6 | 8.11 | 9.45 | 8.10 |
| DPM | 64 | 38.4 | 51.9 | 60.45 | 51.82 |
| Isopar M (EU) | 0 | 0 | 0 | 0.10 | 0.08 |
| Fragrance | 26 | 55.6 | 39.9 | 30 | 40 |

As is shown in the table above, the liquid composition may comprise a third solvent (here: a relatively small amount of Isopar M (EU)).

As is shown in the table above, the liquid composition may comprise a third solvent (here: a relatively small amount of Isopar M (EU)).

Figure 2:
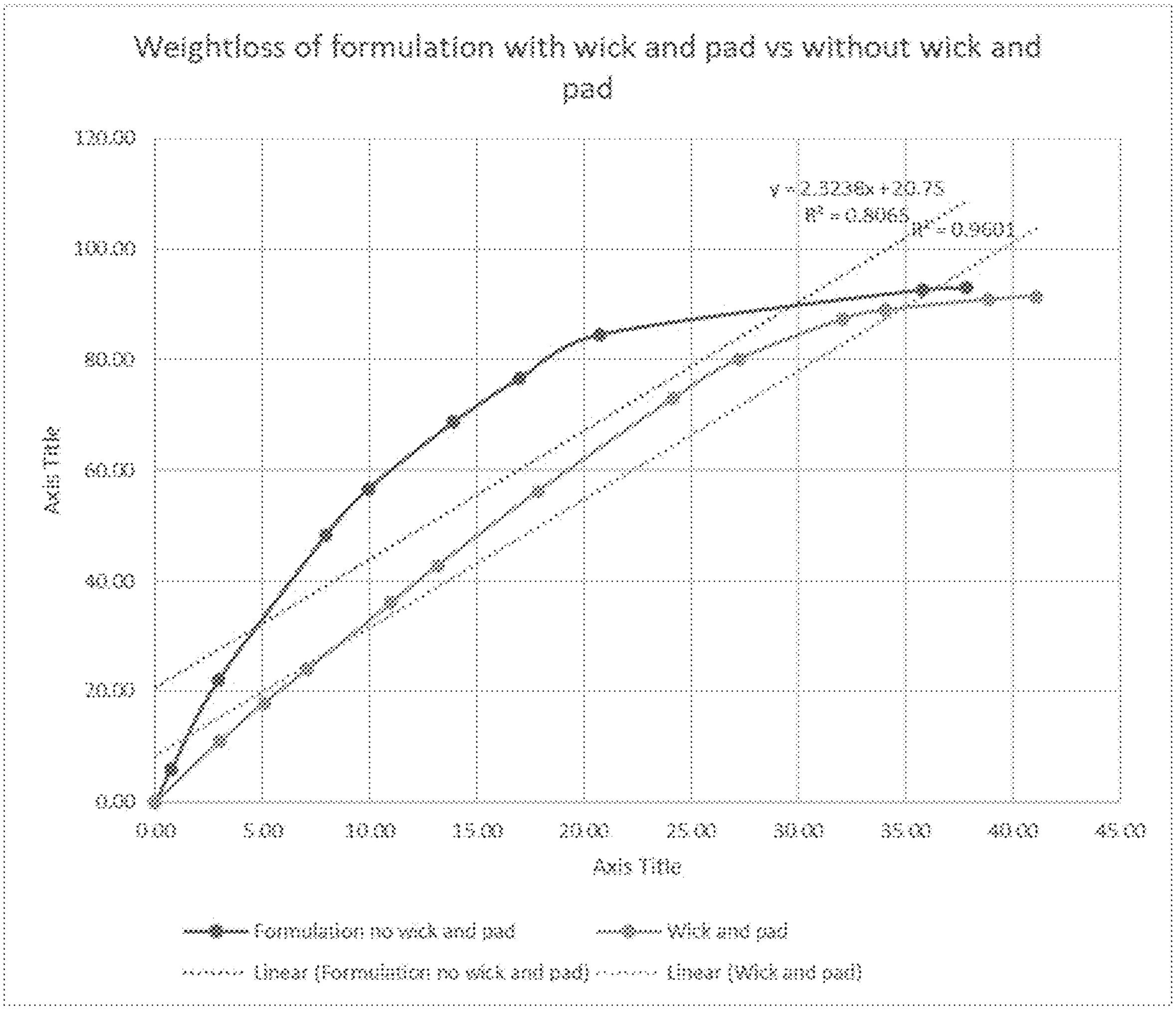
FIG. 2 depicts in a graph the weight loss behavior of a liquid composition over time.

FIG. 2 graphically shows the typical weight loss behaviour of a liquid composition over time according to the examples given above. A comparison of the behaviour with and without wick and membrane is made. The upper solid graph represents the liquid composition which is evaporated over time without a wick and membrane. The liquid composition is in direct contact with surrounding air. It can be seen that a choice of solvents according to the invention already achieves an approximated uniform evaporation profile over a period of time.

The second solid graph below the upper solid graph represents the same liquid composition which is now evaporated including the wick and the membrane such that the liquid composition is evaporated via an outer surface of the membrane.

It can be seen that the second solid graph shows a better linear approximation of weight loss of the liquid composition over an extended period of time as compared to the upper solid graph. This means that the liquid composition has an even more uniform fragrance emanation rate when a wick and a membrane are employed.

For illustration, the graphic also includes dotted graphs showing the linearised upper and second solid graphs. It is evident that the upper solid graph (without wick and membrane) deviates more from the respective linearised graph than the second solid graph (with wick and membrane).

It can thus be concluded that the choice of solvents according to the invention combined with the wick and membrane exhibits a synergistic effect as to achieving a good approximation of a linear weight loss of the liquid composition over time, leading to a uniform evaporation profile and fragrance experience over time.

Figure 3:
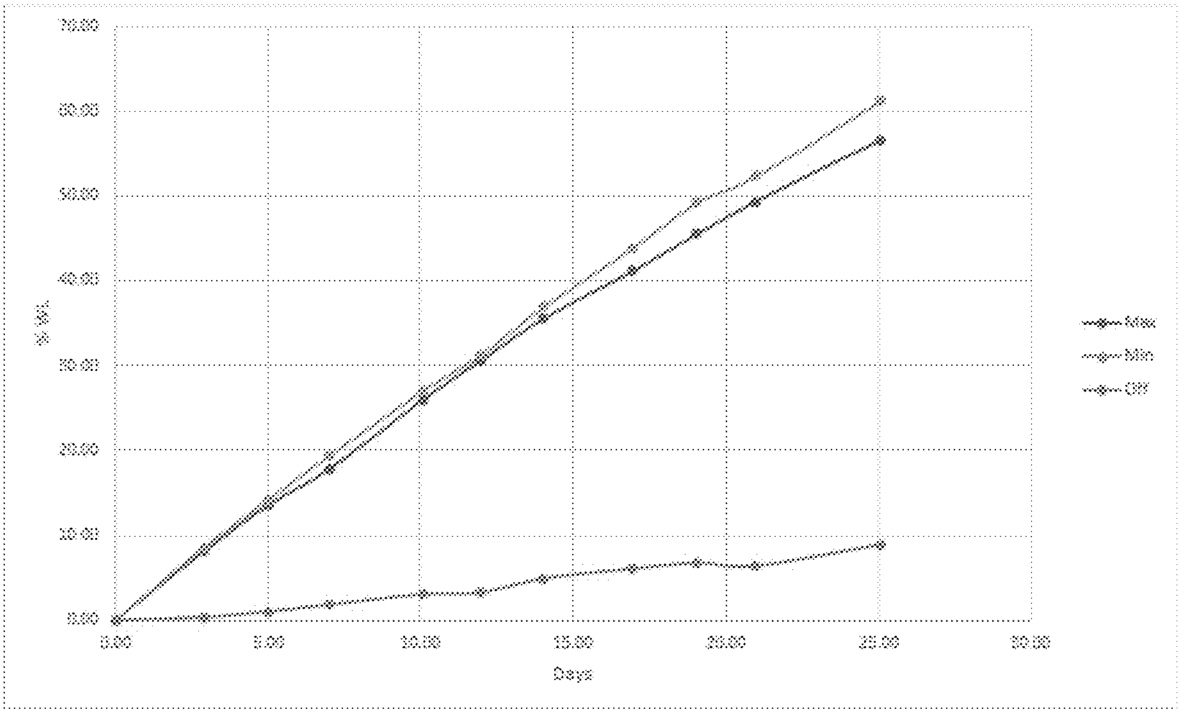
FIG. 3 depicts in a graph weight loss behavior of a liquid composition over time using a passive emanator as described herein.

FIG. 3 graphically shows weight loss curves over time (here: over 25 days) related to a passive emanator including a liquid composition according to the invention and comprising a fragrance in two different fragrance concentrations (referred to as "Min" respectively "Max") as well as a fan for distributing the fragrance. The situation with active fan (see the first and second curves of the graphic) and with inactive fan ("Off", see third curve, at the bottom of the graphic) are described.

The liquid compositions is again a liquid composition comprising DMM and DPM, wherein the weight ratio between DMM and DPM is between 1:5 and 1:7, preferably 1:6, and most preferably 1:6.4.

The first curve ("Min") relates to the liquid composition including the fragrance in a low concentration with the fan in operation.

The second curve ("Max") relates to the liquid composition including the fragrance in a high concentration with the fan in operation.

As can be seen, both first and second curves show a substantially linear weight loss behaviour over time. It can also be seen that the fragrance load has an influence on the steepness of the (substantially linear) weight loss curve. By changing the air flow from the fan directed at the liquid composition, the curve can also be influenced with regard to its steepness. Weighing in one or both of said parameters and selecting them accordingly, a desired weight loss behaviour of the liquid composition over time can be achieved.

The third curve ("Off") relates to the passive emanator including the liquid composition and comprising the fragrance with the fan switched off. As can be seen, the weight loss over time is substantially linear but has much less steepness-which means that significantly less fragrance is distributed to e.g. a room as compared to the situation with the fan switched on (activated fan).

The curves start to plateau towards the end of life (beyond 25 days or many more days, not shown here) of the liquid composition and there are no visible residues in the container of the passive emanator at the end of life.

The invention claimed is:

1. A passive for a liquid composition comprising:

a container including a liquid composition to be evaporated and emanated from the emanator via surrounding air;

a porous wick emerged in the liquid composition; and a porous membrane arranged above a level of the liquid composition, wherein the membrane is in contact with the wick such that the membrane is saturated with the liquid composition via the wick; and, an outer surface of the membrane is in contact with the surrounding air, and wherein the liquid composition comprises:

a first solvent;

a second solvent, and, a fragrance or insect repellent;

wherein the first solvent is Dipropylene Glycol Dimethyl Ether (DMM) and the second solvent is Dipropylene Glycol Monomethyl Ether (DPM), and wherein the DMM and DPM are present in the liquid composition at a respective weight ratio between 1:5 and 1:7.

2. The passive emanator according to claim 1, wherein the membrane covers the liquid composition.

3. The passive emanator according to claim 2, wherein:

the first solvent comprises 5% to 15% by weight, of the liquid composition;

the second solvent comprises 30% to 70% by weight of the liquid composition; and the fragrance or insect repellent comprises 20% to 60% by weight, of the liquid composition.

4. The passive emanator according to claim 1, wherein the first solvent comprises 5% to 15% by weight, of the liquid composition;

the second solvent comprises 30% to 70% by weight, of the liquid composition; and the fragrance or insect repellent comprises 20% to 60% by weight, of the liquid composition.

5. The passive emanator according to claim 1, wherein the wick and the membrane comprise polypropylene (PP) and/or polyethylene (PE) fibres.

6. The passive emanator according to claim 1 wherein the wick and the membrane are hydrophobic.

7. The passive emanator according to claim 1, further comprising a fan, wherein an airflow generated by the fan is directed at the membrane.

8. The passive emanator according to claim 7, wherein the fan is operable at different speeds.

9. The passive emanator according to claim 7, wherein the container, the wick, the membrane and the fan are incorporated into a housing, wherein the housing has at least one inlet opening for attracting air and at least one outlet opening for directing the airflow generated by the fan to the environment.

10. The passive emanator of claim 1, wherein the DMM and DPM are present in the liquid composition at a respective weight ratio between 1:5 and 1:6:4.

11. The passive emanator of claim 10, wherein the DMM and DPM are present in the liquid composition at a respective weight ratio between 1:5 and 1:6.

* * * * *